(12) United States Patent
Tuma et al.

(10) Patent No.: US 7,187,835 B1
(45) Date of Patent: *Mar. 6, 2007

(54) MECHANISMS AND METHODS FOR SELECTIVE WAVELENGTH FILTERING

(75) Inventors: Margaret Tuma, Strongsville, OH (US); Thomas G. Brown, Rochester, NY (US); Russell Gruhlke, Fort Collins, CO (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 94 days.

This patent is subject to a terminal disclaimer.

(21) Appl. No.: 11/044,063

(22) Filed: Jan. 28, 2005

(51) Int. Cl.
G02B 6/10 (2006.01)

(52) U.S. Cl. .................. 385/129; 385/130; 385/131

(58) Field of Classification Search ......... 385/129–131
See application file for complete search history.

(56) References Cited

U.S. PATENT DOCUMENTS

| 5,485,277 A | 1/1996 | Foster |
| 5,809,188 A | 9/1998 | Tseng et al. |
| 5,841,143 A * | 11/1998 | Tuma et al. ............. 250/458.1 |
| 5,986,808 A | 11/1999 | Wang |
| 6,034,809 A | 3/2000 | Anemogiannis |
| 2003/0138208 A1 | 7/2003 | Pawlak et al. |

* cited by examiner

*Primary Examiner*—Jennifer Doan
(74) *Attorney, Agent, or Firm*—Arlene P. Neal; Kent N. Stone; Majid AlBassam

(57) ABSTRACT

An optical filter includes a dielectric waveguide layer, supporting waveguide modes at specific wavelengths and receiving incident light, a corrugated film layer, composed of one of a metal and a semiconductor and positioned adjacent to a second surface of the waveguide layer and a sensor layer, wherein the sensor layer is capable of absorbing optical energy and generating a corresponding electrical signal. The metal film layer supports a plurality of plasmons, the plurality of plasmons producing a first field and is excited by a transverse mode of the waveguide modes at a wavelength interval. The first field penetrates the sensor layer and the sensor layer generates an electrical signal corresponding to an intensity of received incident light within the wavelength interval.

30 Claims, 3 Drawing Sheets

MECHANISMS AND METHODS FOR SELECTIVE WAVELENGTH FILTERING

ORIGIN OF THE INVENTION

The invention described herein was made by employees of the United States Government and may be manufactured and used by or for the Government for Government purposes without payment of any royalties thereon or therefore.

BACKGROUND OF THE INVENTION

1. Field of the Invention

This invention relates to the filtering and detection of light. Specifically, this invention relates to a system and method for enhancing, filtering and sensing light from various sources.

2. Description of Related Art

Optical sensors are essential to performing characterizations of light in many fields. These optical sensors allow for discrimination of light and allow for characterization of an emitting substance based on atomic absorption and emmission lines. However, many of these sensors often suffer from low signal-to-noise ratios, due to low-power optical signals combined with high levels of optical background noise.

Making optical sensors more practical requires increasing the signal-to-noise ratio to provide a detectable signal. This requires either a mechanism to increase the signal or decrease the noise. Generally, optical filters are used, which exhibit a 50% energy loss and are generally broadband.

Miniature optical detectors are currently fabricated using standard silicon processing technology. Examples include semiconductor pn junctions used for optical interconnects and computer chips. Often, these detectors use an optical fiber, so that the radiation is transmitted to a remote detector via the fiber. Such sources increase the optical noise of detection and, thus with increasing detector separation, the signal is generally decreased, and the system complexity is increased, due to additional components.

An additional problem with the prior art is that their systems and methods fail to discriminate between different wavelengths. Each source is characterized by different emission spectrum and reliable analysis of such samples requires wavelength discrimination. Additional filtering components increase costs and may introduce undesirable, thermo-mechanical properties, especially in hostile environments or configurations, requiring miniaturization.

Thus, there is a need in the prior art for means for shielding sensing materials from all but a small wavelength range of radiation. There is also a need for a filtering mechanism to filter all but a few wavelengths of impinging light and that can be easily varied.

SUMMARY OF THE INVENTION

According to one embodiment of the invention, an optical filter is disclosed. The optical filter includes a dielectric waveguide layer, supporting waveguide modes at specific wavelengths and receiving incident light, a corrugated film layer, composed of one of a metal and a semiconductor and positioned adjacent to a second surface of the waveguide layer and a sensor layer, wherein the sensor layer is capable of absorbing optical energy and generating a corresponding electrical signal. The metal film layer supports a plurality of plasmons, the plurality of plasmons producing a first field and is excited by a transverse mode of the waveguide modes at a wavelength interval. The first field penetrates the sensor layer and the sensor layer generates an electrical signal corresponding to an intensity of received incident light within the wavelength interval.

Additionally, the corrugated film layer may be substantially opaque to all wavelengths not within the wavelength interval. The optical filter may also include a dielectric buffer layer, wherein the dielectric buffer layer is interposed between the sensor layer and the corrugated film layer. Alternatively, the plurality of plasmons is positioned at an interface of the corrugated film layer and the buffer layer.

Additionally, the buffer layer may have a uniform thickness across parallel planes which extend parallel with the surface of the corrugated film layer. Also, the sensor layer may be a semiconductor pn junction, wherein the semiconductor pn junction is positioned within the first field. Also, a first area of the corrugated film layer may be corrugated at a first periodicity and a second area of the corrugated film layer may be corrugated at a second periodicity. Each of the surfaces of the corrugated film layer may be composed of a sinusoidal surface relief. Also, the wavelength interval may be approximately 10 nm.

According to another embodiment, an optical filter for filtering light includes a dielectric layer, a metal film layer positioned in optical communication with the dielectric layer, wherein the metal film layer supports at least one plasmon, wherein the at least one plasmon produces a first field and is excited by a transverse mode of waveguide modes at a wavelength interval and a sensor layer, wherein the first field penetrates the sensor layer, whereby the sensor layer absorbs optical energy from the first field and generates a signal corresponding to an intensity of received incident light within the wavelength interval.

According to another embodiment, a method of filtering incident light is disclosed. The method includes the steps of receiving a plurality of wavelengths of incident light at a topmost layer of a filter, inducing a transverse waveguide mode in a dielectric layer based on the light and a periodicity of a grating layer, cross-coupling the traverse waveguide mode to a surface plasmon field between the grating layer and a dielectric layer, absorbing optical energy into a sensor layer based on the cross-coupled surface plasmon field and detecting electrical charges based on the optical absorption of the sensor layer.

These and other variations of the present invention will be described in or be apparent from the following description of the preferred embodiments.

BRIEF DESCRIPTION OF THE DRAWINGS

For the present invention to be easily understood and readily practiced, the present invention will now be described, for purposes of illustration and not limitation, in conjunction with the following figures.

DETAILED DESCRIPTION OF PREFERRED EMBODIMENTS

Previous work in this area relied on surface-plasmon cross-coupling and achieved approximately 100 nm wide cross-coupling regions. The present invention relies on transverse-mode surface-plasmon cross-coupling and achieves cross-coupling regions in the range of 10–50 nm. This allows for a much narrower band of light to couple across the substantially opaque film. The formation of the modes is based on a holographic grating, where by varying the grating periodicity, one can select which wavelengths one wishes to couple across a substantially optically opaque material. The present invention couples a narrow wavelength band across a substantially optically opaque film.

According to one embodiment, by allowing only a narrow wavelength range to couple across, the grating can be used in conjunction with an optical device to selectively detect chemical species, based on the fluorescence of the target material. The detection of various species can be achieved by varying the component materials comprising the device as well as the periodicity of the grating.

Figure 1:
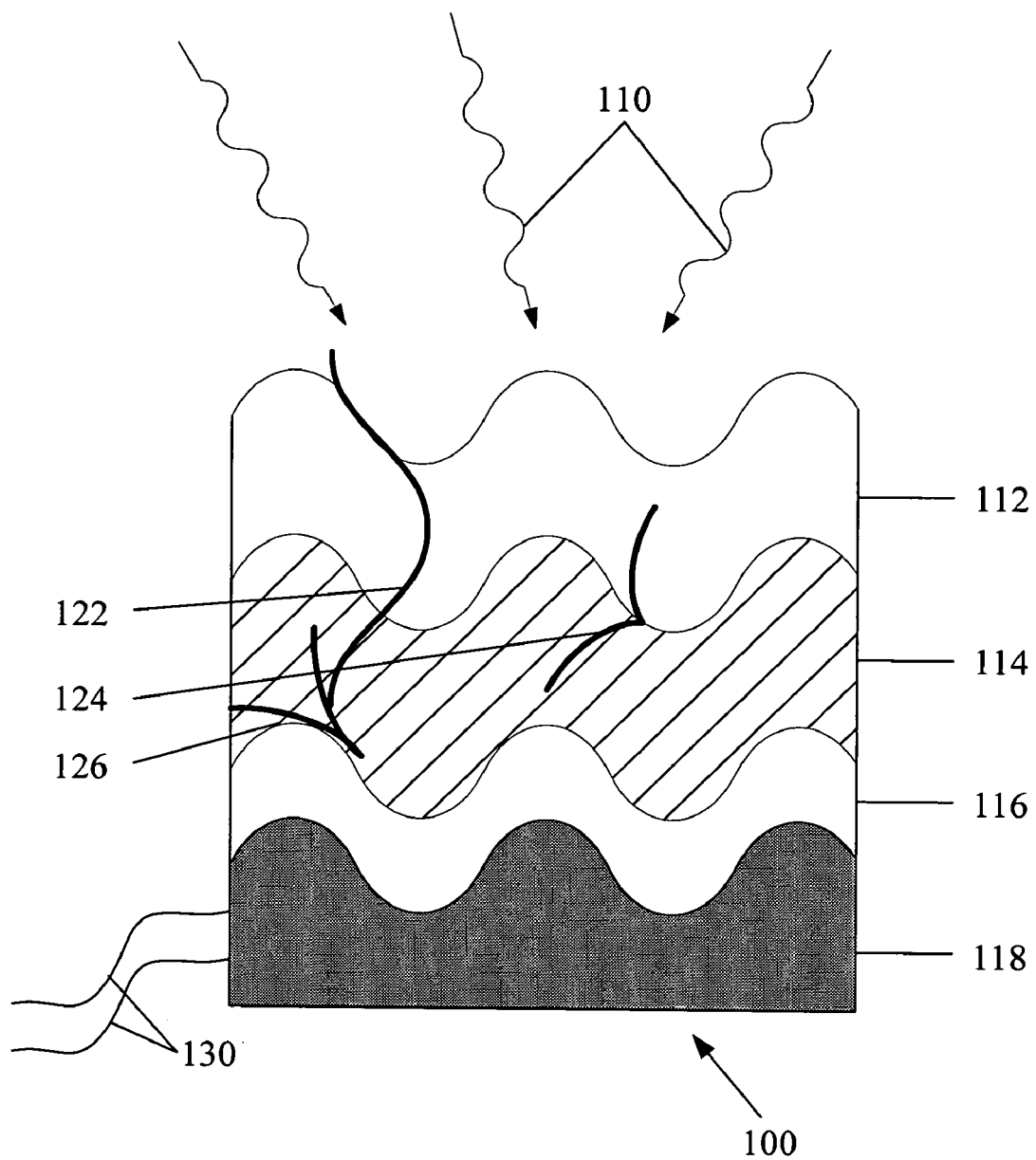
FIG. 1 is a cross-sectional view of the stack of thin dielectric, metal and semiconductor films placed adjacent to some sample material, according to several embodiments of the present invention.

Referring now to FIG. 1, the optical sensor 100 of the present invention is shown. The optical sensor 100 is, according to several embodiments, formed from a stack of thin films. As illustrated, light 110 impinges on the topmost layer of the stack. The topmost layer in the film stack is a dielectric waveguide layer 112. The waveguide layer supports a variety of waveguide modes. For purposes of the specification and claims, waveguide modes are defined as optical excitations confined to the waveguide layer. These waveguide modes have inherent electric and magnetic field profiles which decrease in amplitude with increasing distance from the waveguide layer. Waveguide mode field 122 superimposed over the waveguide layer 112 depicts a decreasing strength of the waveguide mode field as a function of distance from the center of the waveguide layer 112.

The waveguide layer 112 is deposited on an underlying metal film 114. It should be noted that the underlying material need not be metal, as provided in this example, but may be any material that supports surface-plasmons. The metal film 114 is sandwiched between the waveguide layer 112 and an underlying buffer layer 116. Surface plasmons are supported at opposite metal to dielectric interfaces, on both surfaces of the metal film 114. A first plurality of plasmons is supported at the interface of the waveguide layer 112 and the metal or semiconductor film 114. A second plurality of plasmons is supported at interface of the buffer layer 116 and the metal film 114. The surface plasmons are characterized by electric and magnetic fields, the amplitudes of which decay exponentially away from the metal to dielectric interface. The first plurality of plasmons produces a first field 124, the field strength of which is shown graphically decaying from the dielectric waveguide layer to metal film interface. Similarly the second plurality of plasmons produces a second field 126, the field strength of which is shown graphically decaying with distance away from the metal film to buffer layer interface.

The buffer layer 116 is composed of a dielectric material and separates the metal or semiconductor film 114 from a sensor layer 118. The sensor layer is composed of any material having electrical properties affected by the absorption of light. Preferable candidates are semiconductor pn, np or PIN junctions. In these materials light incident the junction, when absorbed, cause an electron transition in the conduction band. The application of a voltage sweeps out this current as a signal. Voltage or resistance changes may also be measured. To measure these electrical signals, electrical leads 130 are supplied in electrical communication with the sensor layer 118.

In several embodiments of the invention, the sensing layer 118, the buffer layer 116, the metal or semiconductor film 114 and the waveguide layer 112 are all corrugated. Corrugation is fabricated directly into either the buffer layer 116 or the sensor layer 118. Corrugation is preferably a sinusoidal surface relief characterized by peak to valley distances of approximately 50 nanometers and by periodicity or pitch distances on the order of one micron. Fabrication of the corrugation may be accomplished by first spinning a photoresist layer on the planar dielectric or sensor layer. The photoresist is then exposed to two interfering laser beams of the same wavelength. This causes a sinusoidal variation in the photoresist exposure. Upon development of the photoresist layer, the variation manifests as a sinusoidal surface relief. This pattern may be transmitted into the dielectric or sensing layer by ion beam milling or dry chemical etching, also known as a reactive ion etching. Additional means of achieving a surface profile in photoresist include exposure using photolithography, electron-beam lithography, flash-imprint lithography or direct laser writing.

When the corrugation is imported into the sensor layer, the dielectric layer can then be deposited onto the sensor layer by several different techniques. Dielectric material such as lithium fluoride or silicon nitride may be deposited by resistive or electron beam evaporation, ion beam or RF sputtering techniques. Polymer and photoresist layers may be deposited by spinning the material onto the underlying sensing layer. The dielectric buffer layer is thin enough, 50 to 100 nanometers, to allow penetration of the second plasmon fields into the sensor layer. In certain embodiments of the invention, the waveguide layer and the buffer layer, positioned on either side of the metal film, are of different materials characterized by different refractive indices. It is also noted that the present invention does not require a buffer layer and is omitted in certain embodiments.

The metal or semiconductor film 114 may be formed by the deposition of metal or semiconducting material on the underlying buffer layer 116. This deposition can be accomplished by electron beam or resistive evaporation, ion beam, RF sputtering or chemical vapor deposition (CVD). The film should be thin enough, approximately 50 nanometers, to conform to the surface relief of the underlying buffer layer 116.

The waveguide layer 122 can be deposited in the same manner as that of the buffer layer 116. Again, materials such as lithium fluoride or silicon nitride may be deposited by resistive or electron beam evaporation, ion beam, RF sputtering or CVD techniques. Polymer and photoresist layers may be deposited by spinning the material onto the underlying layer. According to many embodiments, a typical thickness of the waveguide layer is 200 to 300 nanometers.

Additionally, the area of corrugation does not necessarily need to extend over the entire surface area of the thin film layers. The area of corrugation on the metal or semiconductor film layer acts as a grating which functions as a wavelength discriminator, the function of which is more fully described below. The dielectric and sensor layers need not be corrugated and are corrugated for manufacturing purposes and to structurally support the corrugation of the metal film layer. The area of corrugation on the metal film layer may be any size. The metal or semiconductor film layer may be manufactured with multiple corrugation areas, each with dissimilar periodicities of corrugation. Each area with its characteristic periodicity acts to filter a corresponding wavelength of interest.

The incident light energy is coupled to the waveguide layer to support the propagation of the waveguide modes which generate the strong field. The wavelength content of the resulting waveguide modes is the same as that of the light for which filtering is desired. The plurality of plasmons can act to create a decay pathway through the otherwise substantially opaque metal film layer 114. The metal film layer acts to filter unwanted wavelengths from reaching the sensing material. The second plurality of plasmons generated at the metal film and dielectric buffer layer interface are excited at wavelengths contained in the waveguide modes within the waveguide layer 112.

The presence of a corrugation area within the metal film layer 114 enables the momentum matching of surface plasmons having wavelengths equal to waveguide modes. Over a narrow range of wavelengths, surface plasmon and transverse mode "cross-coupling" occurs and surface plasmons are generated at the metal film 114 and buffer layer 116 interface. Thus over a small wavelength interval optical energy is transmitted across an otherwise substantially opaque thin metal film via the second plurality of plasmons interactions. Only energy at the desired wavelengths is cross-coupled; the natural opacity of the metal film acts to absorb unwanted wavelengths, i.e. noise, thus optimizing or maximizing the signal to noise ratio.

The periodicity of the corrugation determines the wavelength at which the surface plasmons can couple with the transverse mode and therefore also determines the admitted wavelength. The corrugation period needed for a desired wavelength can be calculated. Corrugation areas with periodicities corresponding to desired wavelengths can be incorporated into the metal film layer.

The appropriate parameters are designed to enable SP-TM cross coupling. These parameters include dielectric thickness, index of dielectric, metal thickness, index of metal, grating periodicity, and incident angle of incident light and are related by the following equations. The dispersion equation for surface plasmons is:

$$K_2 = \left(\frac{\omega}{c}\right)\sqrt{\frac{\varepsilon_1 \varepsilon_2}{\varepsilon_1 + \varepsilon_2}} \quad (1)$$

where $\varepsilon_1$ is the dielectric constant for metal and $\varepsilon_2$ is the dielectric constant for the dielectric adjacent to the metal surface.

The dispersion equation for a waveguide mode is:

$$K_{TM} = 2\left(\frac{2\pi}{\lambda}\right) * n_f * h * \cos(\theta_1) - 2\phi_c - 2\phi_s = 2m\pi \quad (2)$$

where $\lambda$ is the wavelength, $n_f$ is the refractive index of the waveguiding layer, h is the thickness of the waveguiding layer, $\theta$ is the angle of total internal reflection (assuming a ray propagation view) and $$\tan(\phi_c) = \sqrt{\frac{(n_f \sin(\theta_1))(n_f \sin(\theta_1)) - n_c * n_c}{(n_f \cos(\theta_1))}} \quad (3)$$

-continued $$\tan(\phi_s) = \sqrt{\frac{(n_f \sin(\theta_1))(n_f \sin(\theta_1)) - n_s * n_s}{(n_f \cos(\theta_1))}} \quad (4)$$

where c refers to the cover medium and s to the substrate medium.

Figure 2:
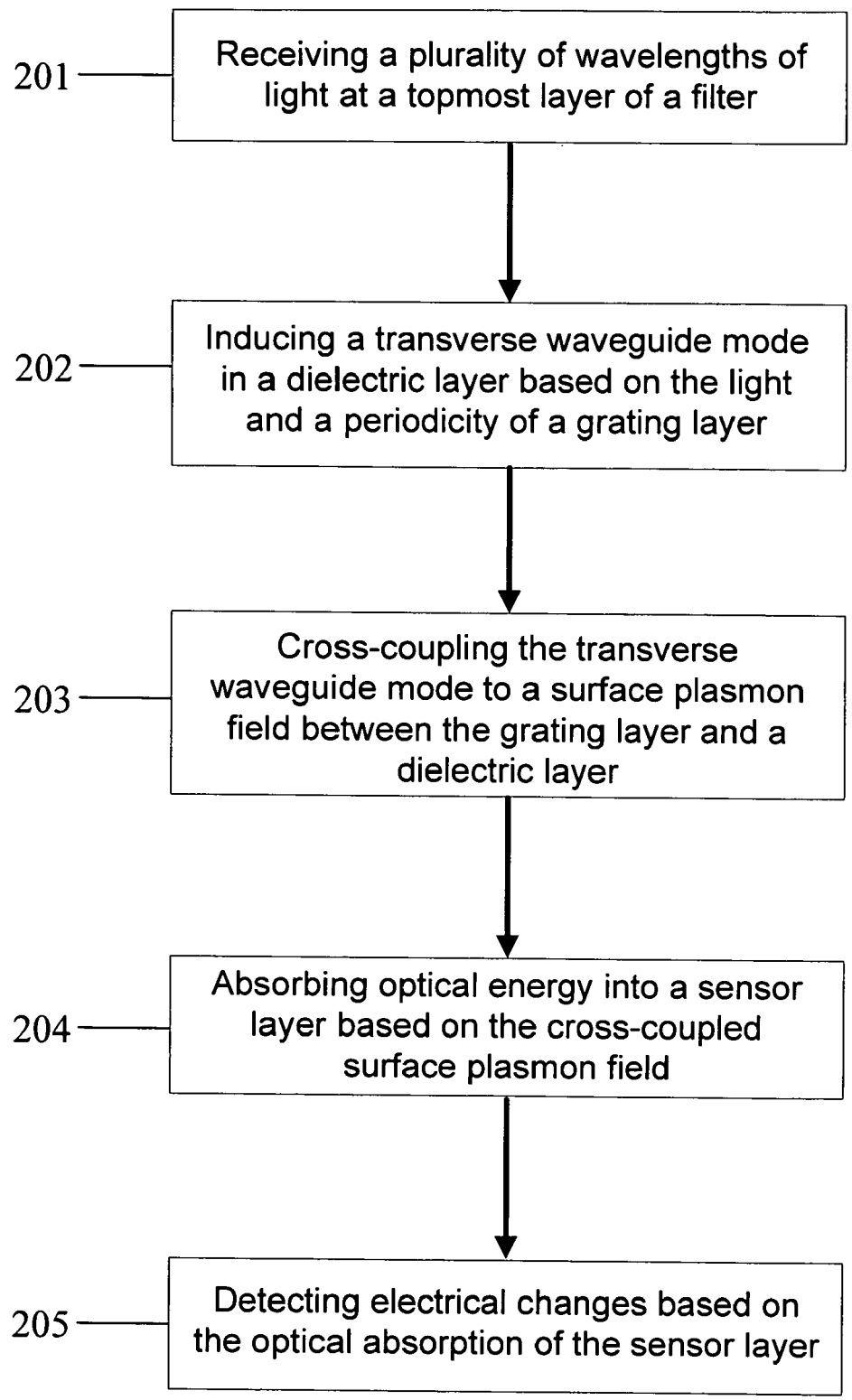
FIG. 2 provides a flowchart showing the process of detecting the fluorescence of a material, according to one embodiment of the present invention.

In addition, the process of optical filtering is illustrated in FIG. 2, according to at least one embodiment of the present invention. In step 201, a plurality of wavelengths of light are received at a topmost layer of a filter. Thereafter, in step 202, a transverse waveguide mode is induced in a dielectric layer based on the light and the periodicity of a grating layer. In step 203, the transverse waveguide mode is cross-coupled to a surface plasmon field between the grating layer and a dielectric layer. Thereafter, optical energy is absorbed into a sensor layer based on the cross-coupled surface plasmon field, in step 204. Finally, in step 205, electrical changes, based on the optical absorption of the sensor layer, are detected.

In preferred embodiments of the invention, the sensing layer is a semiconductor material containing a pn junction. In such embodiments, the absorbed energy generates a conduction band electron. This affects the electrical properties of the sensing layer and can be measured as a current or change in resistance or voltage. This may be used to detect the presence of fluorescent molecules, as discussed below.

Figure 3:
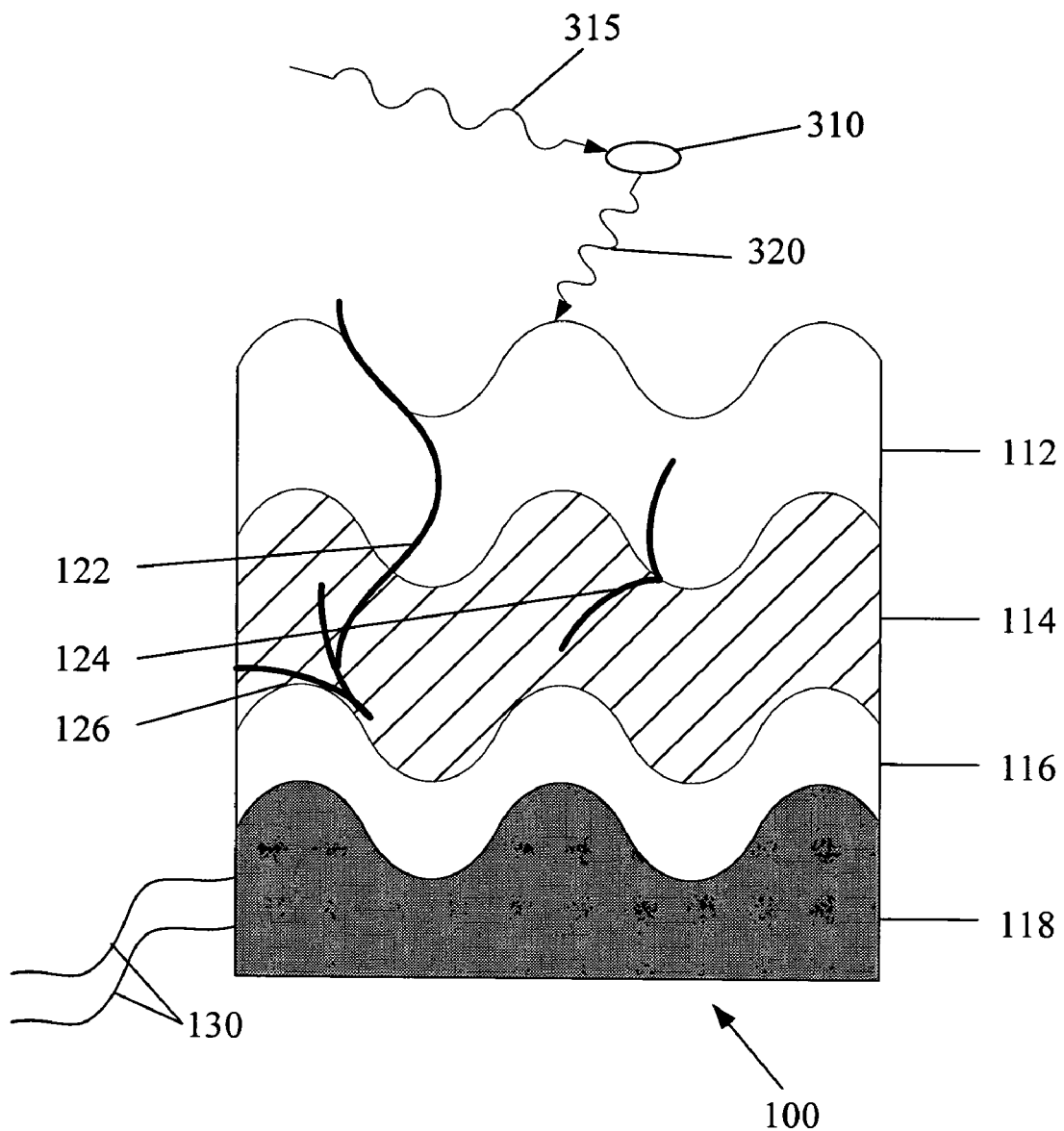
FIG. 3 is a cross-sectional view of the detection of the presence of specific fluorescent molecules, according to an embodiment of the present invention

The invention is also directed to detecting the presence of fluorescent molecules. In this embodiment, as illustrated in FIG. 3, molecules 310 are illuminated 315 and transformed to an excited state. The subsequent relaxation of the molecule into a lower state results in the emission of radiation 320 that can be detected. This electrical signal denotes a fluorescent event occurring in the narrow wavelength range.

Pn, np or PIN type semiconductor materials are formed by a doping process. This art is well known in the semiconductor industry. Atoms such as aluminum or boron are thermally diffused or ion implanted into the intrinsic material such as silicon. It is important that the pn, np or PIN junction fabricated within the sensing layer is located near the surface of the sensor layer within the range of the second field. The second field generated by the second plurality of plasmons can then penetrate the sensor layer to the pn, np or PIN junction.

The present invention allows for narrow wavelength filtering and shielding in a geometry that can be miniaturized and integrated with other active devices. It is also noted that errors may occur if incident light (such as a laser) is too intense and tunnels through the substantially opaque film, washing out the cross-coupled signal. Therefore, care should be taken to avoid having intense light impinge on the topmost layer of the optical sensor.

Although the invention has been described based upon these preferred embodiments, it would be apparent to those skilled in the art that certain modifications, variations, and alternative constructions would be apparent, while remaining within the spirit and scope of the invention. In order to determine the metes and bounds of the invention, therefore, reference should be made to the appended claims.

The invention claimed is:

1. An optical filter for detecting an external light source, comprising:
    a dielectric waveguide layer, supporting waveguide modes at specific wavelengths and receiving incident light on a first surface of the dielectric waveguide layer;

a corrugated film layer, composed of one of a metal and a semiconductor and positioned adjacent to a second surface of said waveguide layer; and a sensor layer, wherein said sensor layer is capable of absorbing optical energy and generating a corresponding electrical signal, wherein said corrugated film layer supports a plurality of plasmons, the plurality of plasmons producing a first field and is resonantly excited by a transverse magnetic mode of the waveguide modes at a wavelength interval, wherein the first field penetrates said sensor layer; and whereby said sensor layer generates an electrical signal corresponding to an intensity of received incident light within the wavelength interval.

2. The optical filter of claim 1, wherein said corrugated film layer is substantially opaque to all wavelengths not within the wavelength interval.

3. The optical filter of claim 1, further comprising a dielectric buffer layer, wherein said dielectric buffer layer is interposed between said sensor layer and said corrugated film layer.

4. The optical filter of claim 3, wherein said plurality of plasmons are positioned at an interface of said corrugated film layer and said buffer layer.

5. The optical filter of claim 1, wherein said buffer layer has a uniform thickness across parallel planes which extend parallel with a surface of said corrugated film layer.

6. The optical filter of claim 1, wherein said sensor layer comprises a semiconductor junction, wherein said semiconductor junction is positioned within the first field.

7. The optical filter of claim 1, wherein at least a first area of said corrugated film layer is corrugated at a first periodicity, wherein at least a second area of said corrugated film layer is corrugated at a second periodicity.

8. The optical filter of claim 1, wherein each surface of said corrugated film layer comprises at least one of a sinusoidal, a triangular or a rectangular surface relief.

9. The optical filter of claim 1, wherein the wavelength interval is less than 50 nm.

10. An optical filter for filtering light comprising:
a dielectric layer;
a metal film layer positioned in optical communication with said dielectric layer, wherein said metal film layer supports at least one plasmon, wherein said at least one plasmon produces a first field and is resonantly excited by a transverse magnetic mode of waveguide modes at a wavelength interval; and
a sensor layer, wherein the first field penetrates said sensor layer, whereby said sensor layer substantially absorbs optical energy from the first field and generates a signal corresponding to an intensity of received incident light within the wavelength interval.

11. The optical filter of claim 10, wherein a first area of said metal film layer is corrugated with a first periodicity, wherein said first area is transparent to all wavelengths within said wavelength interval.

12. The optical filter of claim 10, wherein said metal film layer is substantially opaque to all wavelengths not within said wavelength interval.

13. The optical filter of claim 10, wherein said sensor layer comprises a semiconductor junction, wherein said semiconductor junction is positioned within said first field, and wherein said signal is electrical.

14. The optical filter of claim 10, further comprising a buffer layer, wherein said buffer layer comprises a dielectric material, wherein said buffer layer is interposed between said sensor layer and said metal film layer, and wherein the at least one plasmon is supported at an interface of said buffer layer and said metal film layer.

15. A method of filtering incident light comprising the steps of:
receiving a plurality of wavelengths of incident light at a topmost layer of an optical multilayer;
inducing a transverse waveguide mode in a dielectric layer based on the light and a periodicity of a grating layer;
cross-coupling the traverse waveguide mode to a surface plasmon field between the grating layer and a dielectric layer;
absorbing optical energy into a sensor layer based on the cross-coupled surface plasmon field; and
detecting electrical charges based on the optical absorption of the sensor layer.

16. The method of claim 15, wherein said step of absorbing optical energy comprises absorbing optical energy into a semiconductor pn, np or PIN junction.

17. The method of claim 15, wherein said step of cross-coupling is performed such that the grating layer is substantially opaque to all wavelengths not within a wavelength interval.

18. The method of claim 17, wherein the wavelength interval is less than 50 nm.

19. The method of claim 15, wherein the step of inducing a transverse waveguide mode comprises inducing a transverse waveguide mode in a dielectric layer based on the light, a first periodicity of a first area of the grating layer and a second periodicity of a second area of the grating layer.

20. The method of claim 15, wherein the step of inducing a transverse waveguide mode comprises inducing a transverse waveguide mode in a dielectric layer based on the light and a sinusoidal surface relief pattern of the grating layer.

21. An optical filter for detecting an external light source, comprising:
dielectric waveguide means for guiding incident light, supporting waveguide modes at specific wavelengths and receiving the incident light on a first surface of the dielectric waveguide means;
corrugated film means for supporting a plurality of plasmons, composed of one of a metal and a semiconductor and positioned adjacent to a second surface of said waveguide means; and
sensor means for absorbing optical energy and generating a corresponding electrical signal,
wherein the plurality of plasmons produces a first field and is resonantly excited by a transverse magnetic mode of the waveguide modes at a wavelength interval, wherein the first field penetrates said sensor means; and
whereby said sensor means is configured to generate an electrical signal corresponding to an intensity of received incident light within the wavelength interval.

22. The optical filter of claim 21, wherein said corrugated film means is substantially opaque to all wavelengths not within the wavelength interval.

23. The optical filter of claim 21, further comprising a dielectric buffer means for buffering between said sensor means and said corrugated film means.

24. The optical filter of claim 23, wherein said plurality of plasmons are positioned at an interface of said corrugated film means and said dielectric buffer means.

25. The optical filter of claim 23, wherein said dielectric buffer means has a uniform thickness across parallel planes which extend parallel with a surface of said corrugated film means.

26. The optical filter of claim 21, wherein said sensor means comprises a semiconductor junction means for producing an electrical signal, wherein said semiconductor junction means is positioned within the first field.

27. The optical filter of claim 21, wherein a first area of said corrugated film means is corrugated at a first periodicity, wherein a second area of said corrugated film means is corrugated at a second periodicity.

28. The optical filter of claim 21, wherein each surface of said corrugated film means comprises a sinusoidal, a triangular or a rectangular surface relief.

29. The optical filter of claim 21, wherein the wavelength interval is less than 50 nm.

30. A method of detecting the presence of specific fluorescent molecules, comprising the steps of:

illuminating one or more molecules, such that the molecules are transformed to an excited state;

receiving incident light at a topmost layer of an optical multilayer, the incident light being produced by subsequent relaxation of the molecules at wavelengths characteristic of a chemical composition of the molecules;

inducing a transverse waveguide mode in a dielectric layer based on the light and a periodicity of a grating layer;

cross-coupling the traverse waveguide mode to a surface plasmon field between the grating layer and a dielectric layer;

absorbing optical energy into a sensor layer based on the cross-coupled surface plasmon field; and detecting electrical charges based on the optical absorption of the sensor layer.

* * * * *